(12) United States Patent
Laporte et al.

(10) Patent No.: US 8,222,202 B2
(45) Date of Patent: Jul. 17, 2012

(54) USE OF PEPTIDIC VASOPRESSIN RECEPTOR AGONISTS

(75) Inventors: Regent Laporte, San Diego, CA (US); Pierre J. M. Riviere, San Diego, CA (US)

(73) Assignee: Ferring B.V. (NL)

( * ) Notice: Subject to any disclaimer, the term of this patent is extended or adjusted under 35 U.S.C. 154(b) by 629 days.

(21) Appl. No.: 12/223,673

(22) PCT Filed: Feb. 12, 2007

(86) PCT No.: PCT/IB2007/002248
§ 371 (c)(1), (2), (4) Date: Feb. 3, 2009

(87) PCT Pub. No.: WO2007/144768
PCT Pub. Date: Dec. 21, 2007

(65) Prior Publication Data
US 2009/0305959 A1    Dec. 10, 2009

Related U.S. Application Data

(60) Provisional application No. 60/772,528, filed on Feb. 13, 2006.

(51) Int. Cl.
*A61K 38/11* (2006.01)
*C07K 7/16* (2006.01)

(52) U.S. Cl. ...... 514/1.5; 514/10.9; 514/11.6; 514/15.7; 530/315

(58) Field of Classification Search ............ None
See application file for complete search history.

(56) References Cited

U.S. PATENT DOCUMENTS

| | | | |
|---|---|---|---|
| 4,829,051 A | 5/1989 | Cort et al. | |
| 6,852,697 B1 * | 2/2005 | Mathison et al. | 514/12.2 |
| 2004/0229798 A1 | 11/2004 | Landry et al. | |

FOREIGN PATENT DOCUMENTS

| | | |
|---|---|---|
| GB | 1 076 984 | 7/1967 |
| WO | WO-99/46283 A | 9/1999 |
| WO | WO-03/082334 A | 10/2003 |
| WO | WO-2006/020491 A | 2/2006 |

OTHER PUBLICATIONS

O'Brien et al. Terlipressin for norepinephrine-resistant septic shock. The Lancet. Apr. 6, 2002, vol. 359, pp. 1209-1210.*
Walter, E.; "Therapie des hepatorenalen Syndroms"; Praxis, Schweizerische Rundschau Für Medizin-Inhalt & Zusammenfassungen, vol. 86, No. 4, 1997, Retrieved from the Internet on Jan. 10, 2008 URL:http://www.praxis.ch/content/1997/04__1997.html> abstract.
Döhler, K. D. et al.; "Wirkmechanismen der vasokonstriktiven Therapie der Ösophagusvarizenblutung"; Zeitschrift Für Gastroenterologie, vol. 41, 2003, pp. 1001-1016.

* cited by examiner

*Primary Examiner* — Jeffrey E Russel
(74) *Attorney, Agent, or Firm* — Fish & Richardson P.C.

(57) ABSTRACT

The present invention relates to the use of novel compounds for the manufacture of a medicament for treatment of, inter alia, conditions associated with critical care sepsis, septic shock, hepatorenal syndrome type I, hypertension induced by endstage venal disease, severe burns, thermal injury as well as to a method for treatment of the conditions by administering the compounds. The compounds used are represented by the general formula (1), as further defined in the specification.

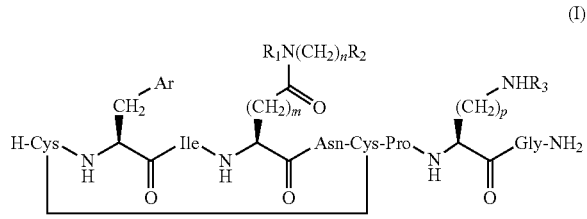

18 Claims, No Drawings

SEQUENCE LISTING

<160> NUMBER OF SEQ ID NOS: 53

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Hgn
<220> FEATURE:
<221> NAME/KEY: MOD_RES
<222> LOCATION: (8)
<223> OTHER INFORMATION: Orn(i-Pr)

<400> SEQUENCE: 1

Cys Phe Ile Xaa Asn Cys Pro Xaa Gly
 1               5

```
<210> SEQ ID NO 2
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Asn((CH2)3OH)
<220> FEATURE:
<221> NAME/KEY: MOD_RES
<222> LOCATION: (8)
<223> OTHER INFORMATION: Orn

<400> SEQUENCE: 2

Cys Phe Ile Asn Asn Cys Pro Xaa Gly
 1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)
<223> OTHER INFORMATION: Dbu

<400> SEQUENCE: 3

Cys Phe Ile Asn Asn Cys Pro Xaa Gly
 1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Asn(CH2CH3)
<220> FEATURE:
<221> NAME/KEY: MOD_RES
<222> LOCATION: (8)
<223> OTHER INFORMATION: Dbu

<400> SEQUENCE: 4

Cys Phe Ile Asn Asn Cys Pro Xaa Gly
 1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)
<223> OTHER INFORMATION: Orn(i-Pr)

<400> SEQUENCE: 5

Cys Phe Ile Gln Asn Cys Pro Xaa Gly
 1               5

<210> SEQ ID NO 6
<211> LENGTH: 9
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (8)
<223> OTHER INFORMATION: Orn(CH2CH3)

<400> SEQUENCE: 6

Cys Phe Ile Gln Asn Cys Pro Xaa Gly
  1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Asn(CH3)2
<220> FEATURE:
<221> NAME/KEY: MOD_RES
<222> LOCATION: (8)
<223> OTHER INFORMATION: Orn

<400> SEQUENCE: 7

Cys Phe Ile Asn Asn Cys Pro Xaa Gly
  1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)
<223> OTHER INFORMATION: Dbu

<400> SEQUENCE: 8

Cys Phe Ile Gln Asn Cys Pro Xaa Gly
  1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Hgn
<220> FEATURE:
<221> NAME/KEY: MOD_RES
<222> LOCATION: (8)
<223> OTHER INFORMATION: Orn

<400> SEQUENCE: 9

Cys Phe Ile Xaa Asn Cys Pro Xaa Gly
  1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (4)
<223> OTHER INFORMATION: Glu(NHOCH3)
<220> FEATURE:
<221> NAME/KEY: MOD_RES
<222> LOCATION: (8)
<223> OTHER INFORMATION: Orn

<400> SEQUENCE: 10

Cys Phe Ile Glu Asn Cys Pro Xaa Gly
  1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Hgn
<220> FEATURE:
<221> NAME/KEY: MOD_RES
<222> LOCATION: (8)
<223> OTHER INFORMATION: Dbu

<400> SEQUENCE: 11

Cys Phe Ile Xaa Asn Cys Pro Xaa Gly
  1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: 4-Pal
<220> FEATURE:
<221> NAME/KEY: MOD_RES
<222> LOCATION: (8)
<223> OTHER INFORMATION: Dbu

<400> SEQUENCE: 12

Cys Xaa Ile Gln Asn Cys Pro Xaa Gly
  1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Ala(4-Thz)
<220> FEATURE:
<221> NAME/KEY: MOD_RES
<222> LOCATION: (8)
<223> OTHER INFORMATION: Dbu

<400> SEQUENCE: 13

Cys Ala Ile Gln Asn Cys Pro Xaa Gly
  1               5

<210> SEQ ID NO 14
<211> LENGTH: 9
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
<222> LOCATION: (8)
<223> OTHER INFORMATION: Dbu

<400> SEQUENCE: 14

Cys Xaa Ile Gln Asn Cys Pro Xaa Gly
  1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: 3-Thi
<220> FEATURE:
<221> NAME/KEY: MOD_RES
<222> LOCATION: (8)
<223> OTHER INFORMATION: Dbu

<400> SEQUENCE: 15

Cys Xaa Ile Gln Asn Cys Pro Xaa Gly
  1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Glu(NHOH)
<220> FEATURE:
<221> NAME/KEY: MOD_RES
<222> LOCATION: (8)
<223> OTHER INFORMATION: Orn

<400> SEQUENCE: 16

Cys Phe Ile Glu Asn Cys Pro Xaa Gly
  1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: 2-Pal
<220> FEATURE:
<221> NAME/KEY: MOD_RES
<222> LOCATION: (8)
<223> OTHER INFORMATION: Dbu

<400> SEQUENCE: 17

Cys Xaa Ile Gln Asn Cys Pro Xaa Gly
  1               5
```

```
<210> SEQ ID NO 18
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: 3-Pal
<220> FEATURE:
<221> NAME/KEY: MOD_RES
<222> LOCATION: (8)
<223> OTHER INFORMATION: Dbu

<400> SEQUENCE: 18

Cys Xaa Ile Gln Asn Cys Pro Xaa Gly
 1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Gln(CH3)
<220> FEATURE:
<221> NAME/KEY: MOD_RES
<222> LOCATION: (8)
<223> OTHER INFORMATION: Orn

<400> SEQUENCE: 19

Cys Phe Ile Gln Asn Cys Pro Xaa Gly
 1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Gln(CH2CH3)
<220> FEATURE:
<221> NAME/KEY: MOD_RES
<222> LOCATION: (8)
<223> OTHER INFORMATION: Orn

<400> SEQUENCE: 20

Cys Phe Ile Gln Asn Cys Pro Xaa Gly
 1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Gln(i-Bu)
<220> FEATURE:
<221> NAME/KEY: MOD_RES
<222> LOCATION: (8)
<223> OTHER INFORMATION: Orn

<400> SEQUENCE: 21
```

```
Cys Phe Ile Gln Asn Cys Pro Xaa Gly
  1               5
```

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Hgn
<220> FEATURE:
<221> NAME/KEY: MOD_RES
<222> LOCATION: (8)
<223> OTHER INFORMATION: Dbu(i-Pr)

<400> SEQUENCE: 22

```
Cys Phe Ile Xaa Asn Cys Pro Xaa Gly
  1               5
```

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Asn(CH2CH2OH)
<220> FEATURE:
<221> NAME/KEY: MOD_RES
<222> LOCATION: (8)
<223> OTHER INFORMATION: Orn

<400> SEQUENCE: 23

```
Cys Phe Ile Asn Asn Cys Pro Xaa Gly
  1               5
```

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Asn(OH)
<220> FEATURE:
<221> NAME/KEY: MOD_RES
<222> LOCATION: (8)
<223> OTHER INFORMATION: Orn

<400> SEQUENCE: 24

```
Cys Phe Ile Asn Asn Cys Pro Xaa Gly
  1               5
```

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)

```
<223> OTHER INFORMATION: Orn

<400> SEQUENCE: 25

Cys Ala Ile Gln Asn Cys Pro Xaa Gly
 1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Dbu

<400> SEQUENCE: 26

Cys Ala Ile Gln Asn Cys Pro Xaa Gly
 1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Asp(CH(CH2OH)2)
<220> FEATURE:
<221> NAME/KEY: MOD_RES
<222> LOCATION: (8)
<223> OTHER INFORMATION: Orn

<400> SEQUENCE: 27

Cys Phe Ile Asp Asn Cys Pro Xaa Gly
 1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Asn(CH2CHOHCH3)
<220> FEATURE:
<221> NAME/KEY: MOD_RES
<222> LOCATION: (8)
<223> OTHER INFORMATION: Orn

<400> SEQUENCE: 28

Cys Phe Ile Asn Asn Cys Pro Xaa Gly
 1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
```

```
<223> OTHER INFORMATION: Asn(CH2CH2OCH2CH2OH)
<220> FEATURE:
<221> NAME/KEY: MOD_RES
<222> LOCATION: (8)
<223> OTHER INFORMATION: Orn

<400> SEQUENCE: 29

Cys Phe Ile Asn Asn Cys Pro Xaa Gly
 1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic  peptide
<220> FEATURE:
<221> NAME/KEY: MOD_RES
<222> LOCATION: (8)
<223> OTHER INFORMATION: Orn

<400> SEQUENCE: 30

Cys Phe Ile Asn Asn Cys Pro Xaa Gly
 1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Asn(CH3)
<220> FEATURE:
<221> NAME/KEY: MOD_RES
<222> LOCATION: (8)
<223> OTHER INFORMATION: Dbu

<400> SEQUENCE: 31

Cys Phe Ile Asn Asn Cys Pro Xaa Gly
 1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Orn(i-Pr)

<400> SEQUENCE: 32

Cys Ala Ile Gln Asn Cys Pro Xaa Gly
 1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
```

```
<223> OTHER INFORMATION: Thi
<220> FEATURE:
<221> NAME/KEY: MOD_RES
<222> LOCATION: (8)
<223> OTHER INFORMATION: Orn

<400> SEQUENCE: 33

Cys Xaa Ile Asn Asn Cys Pro Xaa Gly
 1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
<222> LOCATION: (8)
<223> OTHER INFORMATION: Orn(i-Pr)

<400> SEQUENCE: 34

Cys Xaa Ile Gln Asn Cys Pro Xaa Gly
 1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: 3-Thi
<220> FEATURE:
<221> NAME/KEY: MOD_RES
<222> LOCATION: (8)
<223> OTHER INFORMATION: Orn

<400> SEQUENCE: 35

Cys Xaa Ile Asn Asn Cys Pro Xaa Gly
 1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
<222> LOCATION: (8)
<223> OTHER INFORMATION: Dbu

<400> SEQUENCE: 36

Cys Xaa Ile Asn Asn Cys Pro Xaa Gly
 1               5

<210> SEQ ID NO 37
<211> LENGTH: 9
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (2)
<223> OTHER INFORMATION: 3-Thi
<220> FEATURE:
<221> NAME/KEY: MOD_RES
<222> LOCATION: (8)
<223> OTHER INFORMATION: Dbu

<400> SEQUENCE: 37

Cys Xaa Ile Asn Asn Cys Pro Xaa Gly
 1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Orn

<400> SEQUENCE: 38

Cys Ala Ile Asn Asn Cys Pro Xaa Gly
 1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)
<223> OTHER INFORMATION: Orn(CH3)

<400> SEQUENCE: 39

Cys Phe Ile Gln Asn Cys Pro Xaa Gly
 1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)
<223> OTHER INFORMATION: Orn(CH2CH2CH3)

<400> SEQUENCE: 40

Cys Phe Ile Gln Asn Cys Pro Xaa Gly
 1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)
```

```
<223> OTHER INFORMATION: Orn(i-Pr)

<400> SEQUENCE: 41

Cys Phe Ile Asn Asn Cys Pro Xaa Gly
 1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Orn(i-Pr)

<400> SEQUENCE: 42

Cys Ala Ile Asn Asn Cys Pro Xaa Gly
 1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Thi
<220> FEATURE:
<221> NAME/KEY: MOD_RES
<222> LOCATION: (8)
<223> OTHER INFORMATION: Orn(i-Pr)

<400> SEQUENCE: 43

Cys Xaa Ile Asn Asn Cys Pro Xaa Gly
 1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Ala(2-Fur)
<220> FEATURE:
<221> NAME/KEY: MOD_RES
<222> LOCATION: (8)
<223> OTHER INFORMATION: Dbu

<400> SEQUENCE: 44

Cys Ala Ile Asn Asn Cys Pro Xaa Gly
 1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)
```

```
<223> OTHER INFORMATION: Orn(i-Am)

<400> SEQUENCE: 45

Cys Phe Ile Gln Asn Cys Pro Xaa Gly
  1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)
<223> OTHER INFORMATION: Orn(CH3)

<400> SEQUENCE: 46

Cys Phe Ile Asn Asn Cys Pro Xaa Gly
  1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)
<223> OTHER INFORMATION: Orn(CH2CH3)

<400> SEQUENCE: 47

Cys Phe Ile Asn Asn Cys Pro Xaa Gly
  1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)
<223> OTHER INFORMATION: Orn

<400> SEQUENCE: 48

Cys Phe Ile Asn Asn Cys Pro Xaa Gly
  1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)
<223> OTHER INFORMATION: Asn(CH3)
<220> FEATURE:
<221> NAME/KEY: MOD_RES
<222> LOCATION: (8)
<223> OTHER INFORMATION: Orn

<400> SEQUENCE: 49

Cys Phe Ile Asn Asn Cys Pro Xaa Gly
  1               5
```

```
<210> SEQ ID NO 50
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)
<223> OTHER INFORMATION: Orn(CH2CH2CH3)

<400> SEQUENCE: 50

Cys Phe Ile Asn Asn Cys Pro Xaa Gly
  1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)
<223> OTHER INFORMATION: Orn

<400> SEQUENCE: 51

Cys Phe Ile Gln Asn Cys Pro Xaa Gly
  1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)
<223> OTHER INFORMATION: Hmp
<220> FEATURE:
<221> NAME/KEY: MOD_RES
<222> LOCATION: (4)
<223> OTHER INFORMATION: Hgn
<220> FEATURE:
<221> NAME/KEY: MOD_RES
<222> LOCATION: (8)
<223> OTHER INFORMATION: Dbu(Abu)

<400> SEQUENCE: 52

Xaa Phe Ile Xaa Asn Cys Pro Xaa Gly
  1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)
<223> OTHER INFORMATION: Variable amino acid
```

```
<220> FEATURE:
<221> NAME/KEY: MOD_RES
<222> LOCATION: (8)
<223> OTHER INFORMATION: Variable amino acid

<400> SEQUENCE: 53

Cys Xaa Ile Xaa Asn Cys Pro Xaa Gly
 1               5
```

USE OF PEPTIDIC VASOPRESSIN RECEPTOR AGONISTS

This application is a National Phase of PCT/IB2007/002248, filed Feb. 12, 2007, which claims priority to U.S. Provisional Patent Application 60/772,528, filed Feb. 13, 2006.

FIELD OF THE INVENTION

The present invention relates to the use of novel compounds for the manufacture of a medicament for treatment of inter alia conditions associated with critical care as well as to a method for treatment of said conditions, wherein said compounds are administered.

BACKGROUND

Peptidic vasopressin V1a receptor agonists, such as terlipressin, have recently (see e.g. O'Brian et al., Lancet 359 (9313):1209-10, Jun. 4, 2002) received increased attention for clinical use in treatment of critical care diseases and conditions, including shock of hypovolemic (e.g. hemorrhagic) or vasodilatory (e.g. septic) origin, bleeding esophageal varices (BEV), hepatorenal syndrome (HRS), cardiopulmonary resuscitation and anesthesia-induced hypotension. They have also been shown to have clinical use in the treatment of orthostatic hypotension, paracentesis-induced circulatory dysfunction, intra-operative blood loss and blood loss associated with burn débridement and epistaxis.

In treating critical care conditions it is highly desirable to control the arterial blood pressure, and the drug used is typically administered intravenously. Continuous intravenous drug infusion at increasing or decreasing rates is a practical means of providing the desired degree of control. The attainment of so-called "steady state" plasma concentrations of drug depends on the elimination half life of the drug infused. It is generally recognised that steady state plasma concentration is achieved after a period of time equivalent to three times the elimination half life of the drug. To be practical in a clinical setting the desired arterial blood pressure at the steady state should be attained in about two hours, preferably in one hour or less. V1a agonists with an elimination half life longer than 1 hour are therefore usually not considered useful for critical care treatment.

A disadvantage of terlipressin in many critical care situations is its long duration of action, which makes it difficult to titrate its effect as the disease state changes. Terlipressin metabolites have agonist activity at the human V1a (hV1a) receptor.

Also the compound known as F180 (cf. example 3 in U.S. Pat. No. 5,459,236) has an inconveniently long duration of action to be considered for the treatment of most critical care conditions.

Non-specific receptor agonist activity is the main disadvantage of other existing compounds, e.g. [Phe2,Orn8]OT (cf. example 1f in U.S. Pat. No. 3,352,843) and argininevasopressin (AVP). Activity at related receptors such as V1b, V2 and oxytocin (OT) receptors may potentially generate undesirable side effects and safety concerns. As an example, V2 receptor activation may induce antidiuresis (cf. desmopressin), release of coagulation/thrombolysis factors, and induce vasodilation/hypotension with reflex tachycardia. The latter side effect may also be induced by OT receptor agonist activity.

It is an objective of the present invention to provide use of compounds especially in the treatment of conditions associated with critical care, as well as providing further uses of said compounds.

DISCLOSURE OF THE INVENTION

The present invention relates to the use of compounds represented by the general formula (I) (SEQ ID NO:53):

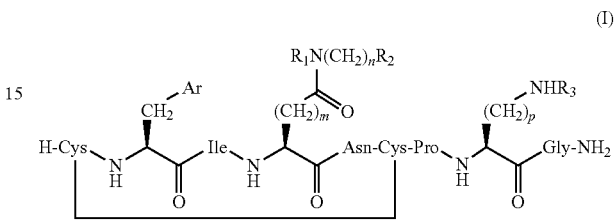

(I)

wherein:
Ar is an aryl group selected from aromatic carbocyclic ring systems, five- or six-membered heteroaromatic ring systems and bicyclic heteroaromatic ring systems;
m is selected from 1, 2 and 3;
n is selected from 0, 1, 2, 3 and 4;
p is selected from 2, 3 and 4;
$R_1$, $R_2$ and $R_3$ are independently selected from H, OH, alkyl, O-alkyl and OC(O)-alkyl;
alkyl is selected from $C_{1-6}$ straight and $C_{4-8}$ branched chain alkyl and optionally has at least one hydroxyl substituent;
and when n=0, $R_1$ and $R_2$ optionally together form a nitrogen containing ring structure comprising from 2 to 5 carbon atoms;
with the proviso that when Ar is phenyl (amino acid no. 2 is Phe), m=2, n=0 and $R_1$=$R_2$=H (amino acid no. 4 is Gln) $R_3$ is not H when p is 3 or 4; and
solvates and pharmaceutically acceptable salts thereof;
for the manufacture of a medicament for treatment of hypertensive gastropathy bleeding, sepsis, severe sepsis, septic shock, prolonged and severe hypotension, intradialytic hypotension, cardiac arrest, trauma related blood loss, vasodilatory shock induced by cardio-pulmonary bypass, milrinone-induced vasodilatory shock in congestive heart failure, late phase hemorrhagic shock, hepatorenal syndrome type I, cardiovascular instability induced by brain death or anaphylactic shock.

Further uses of the above compounds are for the manufacture of a medicament for treatment of hypotension in severe sepsis, acute respiratory distress syndrome (ARDS) or acute lung injury (ALI).

Still further uses of the above compounds are for the manufacture of a medicament for treatment of inadequate tissue oxygenation, e.g. stemming from nitrogen intoxication (hypoxic lactic acidosis) or carbon monoxide intoxication, shock induced by metformin intoxication, mitochondrial disease or cyanide poisoning, vascular leak syndrome (VLS) induced by interleukin-2 (IL-2) or other cytokines, denileukin diftitox or other immunotoxins, or ovarian hyperstimulation syndrome (OHSS), hypertension induced by end-stage renal disease (ESRD), severe burns, thermal injury, irritable bowel disease (IBD), including Crohn's disease and ulcerative colitis, reperfusion injury (e.g. stemming from thrombotic stroke, coronary thrombosis, cardio-pulmonary bypass, coronary artery bypass graft, limb or digit replantation, organ transplantation, bypass enteritis, bypass arthritis, thermal injury, crush injury/ compartment syndrome), infant respiratory distress syndrome (IRDS, RDS), severe acute respiratory syndrome (SARS), ascites, vasodepressor syncope, e.g. vasovagal syncope, postural hypotension with syncope or neurocardiogenic syncope, toxic shock syndrome, idiopathic systemic capillary leak syndrome (Clarkson's disease).

For more detail on the above indications and conditions see e.g. the references Bruha, R. et al. Hepatogastroenterology 49:1161-1166, 2002; Landry, D. W. et al. Circulation 95:1122-1125, 1997; Argenziano, M. et al. Circulation 96:II-286-II-290, 1997; Landry, D. W. et al. U.S. patent application published as no. 2004-229798; Wenzel, V. et al. N. Engl. J. Med. 350:105-113, 2004; Okin, C. R. et al. Obstet. Gynecol. 97:867-872, 2001; Gold, J. et al. Am. J. Cardiol. 85:506-508, 2000; Sharma, R. M. and Setlur, R. Anest. Analg. 101:833-834, 2005; Solanik, P. et al. J. Gastroenterol. Hepatol. 18:152-156, 2000; Yoshioka, T. et al. Neurosurgery 18:565-567, 1986; Kill, C. et al. Int. Arch. Allergy Immunol. 134:260-261, 2004; Westphal, M. et al. Annual Congress of the Society of Critical Care Medicine, Abstract no. 196470, 2006; Landry, D. W. and Oliver, J. A. N. Engl. J. Med. 345(8):588-595, 2001; Baluna, R. and Vitetta, E. S. Immunopharm. 37:117-132, 1997; Delbaere, A. et al. Endocrine. 26:285-290, 2005; Agarwal, R. Cardiol. Clin. 23:237-248, 2005; Demling, R. H. J. Burn Care Rehabil. 26:207-227, 2005; Bonder, C. S. and Kubes, P. Am. J. Physiol. 284:729-733, 2003; Seal, J. B. and Gewertz, B. L. Ann. Vasc. Surg. 19:572-584, 2005; Zoban, P., Cerny, M. Physiol. Res. 52:507-516, 2003; Bermejo, J. F. and Munoz-Fernandez, M. A. Viral Immunol. 17:535-544, 2004; Arroyo, V. Ann. Hepatol. 1:72-79, 2002; Hainsworth, R. Clin. Auton. Res. 14 Suppl 1:18-24, 2004; Chuang, Y. Y. et al. Paediatr. Drugs. 7:11-25, 2005; Cau, C. Minerva Med. 90:391-396, 1999.

Amino acid no. 8 is Orn when $R_3$=H and p=3, and Lys when $R_3$=H and p=4.

For the purposes of the present invention, the following terminology is used.

Aromatic carbocyclic ring systems includes phenyl and naphthyl.

A five-membered heteroaromatic ring system is a monocyclic aromatic ring system having five ring atoms, wherein 1, 2 or 3 ring atoms are independently selected from N, O and S. Preferred such ring systems are selected form a group consisting of thienyl, furyl, pyrrolyl, imidazolyl, thiazolyl, oxazolyl, pyrazolyl, isothiazolyl, isoxazolyl and tetrazolyl.

A six-membered heteroaromatic ring system is a monocyclic aromatic ring system having six ring atoms, wherein 1, 2 or 3 ring atoms are independently selected from N, O and S. It is preferably selected from a group consisting of pyridyl, pyrazinyl, pyrimidinyl, triazinyl and pyridazinyl.

A bicyclic heteroaromatic ring system is a ring system having two five- or six-membered heteroaromatic rings, or a phenyl and a five- or six-membered heteroaromatic ring, or a phenyl and a heterocyclyl ring, or a five- or six-membered heteroaromatic ring and a heterocyclyl ring; connected by a ring fusion, said bicyclic heteroaromatic ring system comprising 8 to 12 ring atoms, wherein 1, 2 or 3 of the ring atoms are independently selected from N, O and S. It is preferably selected from a group consisting of indole, quinoline, tetrahydroquinoline, isoquinoline, tetrahydroisoquinoline, 1,4-benzodioxan, coumarin, benzofuran, 1,2-benzisoxazole, benzothiophene, benzoxazole, benzthiazole, benzimidazole, benztriazole, pyrolizidine and quinolizidine.

A heterocyclyl or heterocyclic moiety is a saturated or partially saturated ring system having 3 to 7 ring atoms, wherein 1, 2 or 3 ring atoms are independently selected from N, O and S. Heterocyclyl moieties are preferably selected from a group consisting of aziridine, oxirane, thiirane, azetidine, oxetane, thietane, pyrrolidine, pyrroline, imidazolidine, pyrazolidine, dioxolane, tetrahydrofuranyl, piperidine, piperazine, morpholine, tetrahydropyranyl, 1,4-dioxanyl, homopiperidinyl, homopiperazinyl and hexamethylene oxide.

It deserves mentioning that e.g. also isopropyl and 2-n-butyl groups are encompassed by the expression $C_{1-6}$ straight chain alkyl, as said expression is not related to the binding site of the straight chain in question.

$C_{1-6}$ denotes having from one to six carbon atoms, including any number therebetween, and this nomenclature is used analogously herein.

Examples of pharmaceutically acceptable salts comprise acid addition salts, e.g. a salt formed by reaction with hydrohalogen acids, such as hydrochloric acid, and mineral acids, such as sulphuric acid, phosphoric acid and nitric acid, as well as aliphatic, alicyclic, aromatic or heterocyclic sulphonic or carboxylic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, toluenesulphonic acid and naphthalenesulphonic acid.

Ar is preferably selected from phenyl, 2- or 3-thienyl, 2- or 3-furyl, 2-, 3- or 4-pyridyl and 2-, 4- or 5-thiazolyl. It is particularly preferred that $R_1$ is H.

In preferred embodiments p is 2 or 3.

It is preferred to select $R_2$ from H, OH, $CH_3$, $CH_2CH_3$, $CH(CH_3)_2$, $CH(CH_2OH)_2$, $CH(OH)CH_3$ (both enantiomers), $OCH_3$ and $OCH_2CH_2OH$.

Moreover, it is preferred to select $R_3$ from H, methyl, ethyl, n-propyl, i-propyl and i-amyl.

In the most preferred embodiment of the present use, said compound having the formula (I) is selected from a group consisting of:

(1)

H-Cys-Phe-Ile-Hgn-Asn-Cys-Pro-Orn(i-Pr)-Gly-NH₂;

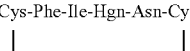

(SEQ ID NO: 1)

(2)

H-Cys-Phe-Ile-Asn((CH₂)₃OH)-Asn-Cys-Pro-Orn-Gly-NH₂;

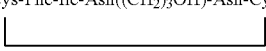

(SEQ ID NO: 2)

(3)

H-Cys-Phe-Ile-Asn-Asn-Cys-Pro-Dbu-Gly-NH₂;

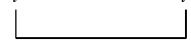

(SEQ ID NO: 3)

(4)

H-Cys-Phe-Ile-Asn(CH₂CH₃)-Asn-Cys-Pro-Dbu-Gly-NH₂;

(SEQ ID NO: 4)

(5)

H-Cys-Phe-Ile-Gln-Asn-Cys-Pro-Orn(i-Pr)-Gly-NH₂;

(SEQ ID NO: 5)

H-Cys-Phe-Ile-Gln-Asn-Cys-Pro-Orn(CH$_2$CH$_3$)-Gly-NH$_2$;　(6)
　　　|_____|

(SEQ ID NO: 6)

H-Cys-Phe-Ile-Asn-(CH$_3$)$_2$-Asn-Cys-Pro-Orn-Gly-NH$_2$.　(7)
　　　|_____|

(SEQ ID NO: 7)

The number in parenthesis denotes the compound as referred to in the following.

The pharmaceutical composition used when practising the present invention may be adapted for oral, intravenous, topical, intraperitoneal, nasal, buccal, sublingual or subcutaneous administration or for administration via the respiratory tract e.g. in the form of an aerosol or an air-suspended fine powder. The composition may thus for instance be in the form of tablets, capsules, powders, microparticles, granules, syrups, suspensions, solutions, transdermal patches or suppositories.

The pharmaceutical composition used may optionally comprise e.g. at least one further additive selected from a disintegrating agent, binder, lubricant, flavoring agent, preservative, colorant and any mixture thereof. Examples of such and other additives are found in "*Handbook of Pharmaceutical Excipients*"; Ed. A. H. Kibbe, 3$^{rd}$ Ed., American Pharmaceutical Association, USA and Pharmaceutical Press UK, 2000.

The pharmaceutical composition used is most preferably adapted for parenteral administration. It may comprise a sterile aqueous preparation of the compounds of the invention preferably isotonic with the blood of the recipient. This aqueous preparation may be formulated according to known methods using suitable dispersing or wetting agents and suspending agents. Illustrative of a preparation produced in such conventional fashion is the aqueous formulation, Remestyp® (terlipressin). The preparation also may be a sterile injectable solution or suspension in a diluent or solvent, for example as a solution in 1,3-butane diol. Water, Ringer's solution, and isotonic sodium chloride solution are exemplary acceptable diluents. Sterile, fixed oils may be employed as a solvent or suspending medium. Bland fixed oils, including synthetic mono or di-glycerides, and fatty acids, such as oleic acid, may also be used.

In another embodiment the invention relates to a method for treatment of hypertensive gastropathy bleeding, sepsis, severe sepsis, septic shock, prolonged and severe hypotension, intradialytic hypotension, cardiac arrest, trauma related blood loss, vasodilatory shock induced by cardio-pulmonary bypass, milrinone-induced vasodilatory shock in congestive heart failure, hepatorenal syndrome type I, anaphylactic shock, or cardiovascular instability induced by brain death, wherein said method comprises administering to an animal, including human, patient of a therapeutically effective amount of a compound as outlined above.

In a further embodiment the invention relates to a method for treatment of hypotension in severe sepsis, acute respiratory distress syndrome or acute lung injury, wherein said method comprises administering to an animal, including human, patient of a therapeutically effective amount of a compound as outlined above.

In another embodiment the invention relates to a method for treatment of inadequate tissue oxygenation, shock induced by metformin intoxication, mitochondrial disease or cyanide poisoning, vascular leak syndrome induced by interleukin-2 or other cytokines, denileukin diftitox or other immunotoxins, or ovarian hyperstimulation syndrome, hypertension induced by end-stage renal disease, severe burns, thermal injury, irritable bowel disease, ulcerative colitis, reperfusion injury, infant respiratory distress syndrome, severe acute respiratory syndrome, ascites, vasodepressor syncope, including vasovagal syncope, postural hypotension with syncope or neurocardiogenic syncope, toxic shock syndrome, idiopathic systemic capillary leak syndrome (Clarkson's disease), wherein said method comprises administering to an animal, including human, patient of a therapeutically effective amount of a compound as outlined above.

The typical dosage of the compounds used according to the present invention varies within a wide range and will depend on various factors such as the individual needs of each patient and the route of administration. The dosage administered by infusion is generally within the range of 0.01-200 µg/kg body weight per hour. A physician of ordinary skill in the art will be able to optimise the dosage to the situation at hand.

| The abbreviations used are: | |
|---|---|
| Abu | 2-aminobutyric acid |
| Boc | tert-butoxycarbonyl |
| BOP | benzotriazol-1-yloxy trisdimethylamino-phosphonium hexafluorophosphate |
| Dbu | 2,4-diaminobutyric acid |
| DCC | N,N'-dicyclohexylcarbodiimide |
| DCHA | dicyclohexylamine |
| DCM | dichloromethane |
| DIAD | diisopropyl diazodicarboxylate |
| DIC | N,N'-diisopropylcarbodiimide |
| DIEA | N,N-diisopropyl-N-ethylamine |
| DMF | N,N-dimethylformamide |
| Fm | 9-fluorenylmethyl |
| Fmoc | 9-fluorenylmethoxycarbonyl |
| Hgn | homoglutamine |
| Hmp | 2-hydroxy-3-mercaptopropionic acid |
| HOBt | 1-hydroxybenzotriazole |
| HPLC | high performance liquid chromatography |
| i | iso |
| Mmt | 4-methoxytrityl |
| Mob | p-methoxybenzyl |
| MS | mass spectrometry |
| Orn | ornithine |
| Ph | phenyl |
| Pr | propyl |
| PyBOP | benzotriazol-1-yloxy trispyrrolidine-phosphonium hexafluorophosphate |
| o-NBS-Cl | 2-nitrobenzenesulfonyl chloride |
| OT | oxytocin |
| Rt | retention time |
| TFA | trifluoroacetic acid |
| TIS | triisopropylsilane |
| TMOF | trimethylorthoformate |
| TPP | triphenylphosphine |
| Trt | trityl |
| VT | vasotocin, [Ile$^3$]vasopressin |

Unless otherwise specified L-amino acids were used, and conventional amino acid terminology is adhered to.

Experimental (Synthesis)

Amino acid derivatives and resins were purchased from commercial providers (Novabiochem, Bachem Peptide International and PepTech Corporation). Fmoc-Hgn-OH was synthesised according to literature (Wisniewski, K., Kolodziejczyk, A. S. *Org. Prep. Proced. Int.* 1997, 29, 338-341). Other chemicals and solvents were provided from Sigma-Aldrich, Fisher Scientific and VWR.

The compounds herein were synthesised by standard methods in solid phase peptide chemistry utilising both Fmoc and Boc methodology. Unless otherwise provided, all reactions were performed at room temperature. In addition to the references cited supra, the following standard reference literature provides further guidance on general experimental set up, as well as on the availability of required starting material and reagents:

Kates, S. A., Albericio, F., Eds., *Solid Phase Synthesis. A Practical Guide*, Marcel Dekker, New York, Basel, 2000;

Stewart, J. M., Young, J. D. *Solid Phase Synthesis*, Pierce Chemical Company, 1984;

Bisello, et al., *J. Biol. Chem.* 1998, 273, 22498-22505; and

Merrifield, *J. Am. Chem. Soc.* 1963, 85, 2149-2154.

Purity of the synthesized peptide may be determined by analytical reversed phase HPLC. Structural integrity of the peptides may be confirmed using amino acid analysis and electrospray mass spectrometry.

The peptides synthesised by Fmoc methodology were cleaved with a TFA/TIS/H$_2$O 96/2/2 (v/v/v) solution, and cleavage in Boc methodology was accomplished with 90% HF/10% anisole (v/v) solution. Disulfide bridge (ring) formation was achieved by oxidation of linear peptides dissolved in 10% TFA (aq) with iodine. Peptides were purified by preparative HPLC in triethylammonium phosphate buffers (aq). The compounds were finally converted to acetate salts using conventional HPLC methodology. The fractions with a purity exceeding 97% were pooled and lyophilised.

Synthesis of Peptides with Alkylated Side Chain in Position No. 8:

The peptides were assembled with Fmoc methodology. The diamino acid residue in position no. 8 was introduced with an acid labile (i.e. removable with a solution containing 1-2% TFA) protecting group, such as methoxytrityl (Mmt; see Barlos, K. et al. in *Peptides* 1992, Schneider, C. H., Eberle, A. N., Eds., ESCOM Science Publishers B. V., 1993, pp 283-284). Resin bound peptide was treated with a DCM/TIS/TFA 93/5/2 (v/v/v) solution for the Mmt group removal. Reductive alkylation with acetone/NaBH(OAc)$_3$ provided the N-isopropyl peptide.

To avoid undesirable N,N-dialkylation in reductive alkylation in the above procedure, which may occur when straight chain alkyl aldehydes are used, an alternative was developed, wherein after the Mmt removal the amino group was first derivatised with 2-nitrobenzenesulfonyl chloride (o-NBS—Cl; see Fukuyama, T.; Jow, C.-K.; Cheung, M. *Tetrahedron Lett.* 1995, 36, 6373-6374). The resulting sulphonamide was then alkylated with an appropriate alcohol under conventional Mitsunobu reaction conditions, typically utilising TPP/DIAD in 1,2-dimethoxyethane (Mitsunobu, O. *Synthesis* 1981, 1-28). The o-NBS—Cl group was subsequently removed with 5% potassium thiophenolate in DMF, after which the peptide was cleaved from the resin.

Synthesis of Peptides with N-Alkylated Side Chain in Position No. 4:

The peptides were assembled with Boc methodology. The residue in position no. 4 was introduced in the sequence as Boc-Asp(OFm)—OH. After complete peptide assembly the side chain protection was removed with 30% piperidine in DMF. The resulting free carboxylic group was converted to the desired amide by coupling with an appropriate amine mediated by PyBOP or BOP/DIEA. The N-terminal Boc group was then removed, followed by HF cleavage, cyclisation and purification by HPLC.

Table 1 lists the compounds prepared by the above procedure. $R_1$ is H for all compounds except no. 7, where $R_1$ is $CH_3$. An asterisk "*" marks the most preferred embodiments.

TABLE 1

Compounds prepared with the formula (I)

| Ar | m | n | $R_2$ | p | $R_3$ | Denoted SEQ ID NO: |
|---|---|---|---|---|---|---|
| Ph | 2 | 0 | H | 2 | H | 8 |
| Ph | 3 | 0 | H | 3 | H | 9 |
| Ph | 2 | 0 | OCH$_3$ | 3 | H | 10 |
| Ph | 3 | 0 | H | 2 | H | 11 |
| 4-pyridyl | 2 | 0 | H | 2 | H | 12 |
| 4-thiazolyl | 2 | 0 | H | 2 | H | 13 |
| 2-thienyl | 2 | 0 | H | 2 | H | 14 |
| 3-thienyl | 2 | 0 | H | 2 | H | 15 |
| Ph | 2 | 0 | OH | 3 | H | 16 |
| 2-pyridyl | 2 | 0 | H | 2 | H | 17 |
| 3-pyridyl | 2 | 0 | H | 2 | H | 18 |
| Ph | 2 | 0 | CH$_3$ | 3 | H | 19 |
| Ph | 2 | 1 | CH$_3$ | 3 | H | 20 |
| Ph | 2 | 1 | CH(CH$_3$)$_2$ | 3 | H | 21 |
| Ph | 3 | 0 | H | 3 | CH(CH$_3$)$_2$ | 1* |
| Ph | 3 | 0 | H | 2 | CH(CH$_3$)$_2$ | 22 |
| Ph | 1 | 2 | OH | 3 | H | 23 |
| Ph | 1 | 0 | OH | 3 | H | 24 |
| 2-furyl | 2 | 0 | H | 3 | H | 25 |
| Ph | 1 | 3 | OH | 3 | H | 2* |
| 2-furyl | 2 | 0 | H | 2 | H | 26 |
| Ph | 1 | 0 | CH(CH$_2$OH)$_2$ | 3 | H | 27 |
| Ph | 1 | 1 | CH(OH)CH$_3$ | 3 | H | 28 |
| Ph | 1 | 2 | OCH$_2$CH$_2$OH | 3 | H | 29 |
| Ph | 1 | 0 | H | 3 | H | 30 |
| Ph | 1 | 0 | H | 2 | H | 3* |
| Ph | 1 | 0 | CH$_3$ | 2 | H | 31 |
| Ph | 1 | 1 | CH$_3$ | 2 | H | 4* |
| 2-furyl | 2 | 0 | H | 3 | H | 32 |
| 2-thienyl | 1 | 0 | H | 3 | H | 33 |
| Ph | 2 | 0 | H | 3 | CH(CH$_3$)$_2$ | 5* |
| 2-thienyl | 2 | 0 | H | 3 | CH(CH$_3$)$_2$ | 34 |
| 3-thienyl | 1 | 0 | H | 3 | H | 35 |
| 2-thienyl | 1 | 0 | H | 2 | H | 36 |
| 3-thienyl | 1 | 0 | H | 2 | H | 37 |
| 2-furyl | 1 | 0 | H | 3 | H | 38 |
| Ph | 2 | 0 | H | 3 | CH$_3$ | 39 |
| Ph | 2 | 0 | H | 3 | CH$_2$CH$_2$CH$_3$ | 40 |
| Ph | 1 | 0 | H | 3 | CH(CH$_3$)$_2$ | 41 |
| 2-furyl | 1 | 0 | H | 3 | CH(CH$_3$)$_2$ | 42 |
| 2-thienyl | 1 | 0 | H | 3 | CH(CH$_3$)$_2$ | 43 |
| 2-furyl | 1 | 0 | H | 2 | H | 44 |
| Ph | 2 | 0 | H | 3 | CH$_2$CH$_3$ | 6* |
| Ph | 2 | 0 | H | 3 | (CH$_2$)$_2$CH(CH$_3$)$_2$ | 45 |
| Ph | 1 | 0 | H | 3 | CH$_3$ | 46 |
| Ph | 1 | 0 | H | 3 | CH$_2$CH$_3$ | 47 |
| Ph | 1 | 0 | CH$_3$ | 3 | H | 7* |
| Ph | 1 | 1 | CH$_3$ | 3 | H | 48 |
| Ph | 1 | 0 | CH$_3$ | 3 | H | 49 |
| Ph | 1 | 0 | H | 3 | CH$_2$CH$_2$CH$_3$ | 50 |

The following detailed examples are provided to further illustrate the synthesis:

Compound 1; [Phe$^2$,Hgn$^4$,Orn(i-Pr)$^8$]VT:

The amino acid derivatives used were Boc-Cys(Trt)-OH, Fmoc-Phe-OH, Fmoc-Ile-OH, Fmoc-Hgn-OH, Fmoc-Asn (Trt)-OH, Fmoc-Cys(Trt)-OH, Fmoc-Pro-OH, Fmoc-Orn (Mmt)-OH and Fmoc-Gly-OH. Fmoc-Hgn-OH was synthesised as mentioned above. Analytical HPLC was performed on a Waters 600 Liquid Chromatograph using a Vydac C18, 5µ 4.6×250 mm, column at a flow rate of 2 ml/min. Preparative HPLC was performed on a Waters 2000 Liquid Chromatograph using a Prepak 47×300 mm cartridge at a flow rate of 100 ml/min. Final compound analysis was performed on a 1100 Agilent Liquid Chromatograph using a Vydac C18, 5µ 2.1×250 mm, column at a flow rate of 0.3 ml/min. Mass spectra were recorded on a Finnigan MAT spectrometer.

The fully protected peptide resin was synthesised on an Applied Biosystems 9050 Peptide Synthesiser starting from 2 g (0.5 mmol) of Tentagel-S-RAM resin (Peptides International). DIC/HOBt mediated single couplings with a 4-fold excess of amino acid derivatives were performed. The Fmoc group was removed with 20% piperidine in DMF. Upon completion of the automated synthesis, the resin was transferred into a manual synthesis vessel and was treated with DCM/TIS/TFA 93/5/2 (v/v/v) solution (30 ml) for 2×1.5 hours for removal of the Mmt group. The resin was thoroughly washed with DCM and was subsequently suspended in 15 ml of 1,2-dichloroethaneTMOF 1:1 (v/v). 0.2 ml of acetone was then added followed by 0.6 g of $NaBH(OAc)_3$. The suspension was shaken overnight and the resin was washed with methanol, DMF and DCM and dried in vacuo. The resin was then treated with 30 ml of the $TFA/TIS/H_2O$ 96/2/2 (v/v/v) solution for 1.5 hours and filtered off. The filtrate was evaporated and the crude linear peptide was precipitated with diethyl ether. The precipitate was immediately dissolved in 500 ml of 10% TFA (aq), and the peptide was oxidised by adding 0.1 M $I_2$ in methanol to the magnetically stirred solution until yellow color persisted. Excess of iodine was reduced with ascorbic acid. The reaction mixture was then cooled with crushed ice and pH was adjusted to about 5 by adding concentrated ammonia (aq). The mixture was loaded onto an HPLC column and purified using a triethylammonium phosphate buffer with pH 5.2. The compound was eluted with a gradient of acetonitrile. The fractions with a purity exceeding 97% were pooled, and the resulting solution was diluted with 2 volumes of water. The solution was reloaded onto the column which was then washed with 2 l of 0.1 M ammonium acetate (aq) and equilibrated with 2% acetic acid (aq). The compound was eluted with a fast (3%/min) gradient of acetonitrile. The fractions containing the desired product were pooled and lyophilised. 168 mg (.about.30% yield) of white amorphous powder was obtained. HPLC: Rt=8.5 min, gradient: 20→40% B over 20 min, t=40° C., solvent A 0.01% TFA (aq), solvent B 70% $CH_3CN$, 0.01% TFA (aq); Purity: 98.8%; MS ($M+H^+$): expected 1048.5, observed 1048.5.

Compound 4; [$Phe^2,Asn(Et)^4, Dbu^8$]VT:

The amino acid derivatives used were Boc-Cys(Mob)-OH, Boc-Phe-OH, Boc-Ile-OH, Boc-Asp(OFm)-OH, Boc-Asn-OH, Boc-Pro-OH, Boc-Dbu(benzyloxycarbonyl)-OH DCHA salt and Boc-Gly-OH, all purchased from Novabiochem and Bachem. HPLC and MS operations were performed as in the synthesis of compound 1.

The fully protected peptide resin was manually synthesised starting from 0.6 g (0.4 mmol) of 4-methyl-benzhydrylamine resin (Novabiochem). DCC, PyBOP or DIC/HOBt mediated single couplings with 2.5-fold excess of amino acid derivatives were employed. The Boc group was removed with 50% TFA in DCM containing 1% of m-cresol. Upon completion of the synthesis, the 9-fluorenylmethyl ester was removed from the β-carboxylic group of aspartic acid by treatment with 30% piperidine in DMF for 2×30 min. The resin was washed with 1 M HOBt in DMF solution for 30 min and then twice with DMF only. The free carboxylic group was amidated by overnight treatment with 2 mmol of ethylamine/PyBOP/DIEA in DMF. The finished resin was washed with methanol, DMF and DCM and dried in vacuo. The peptide was cleaved from the resin by using 30 ml of anhydrous HF containing 3 ml of anisole at 0° C. for 90 minutes. The HF was evaporated off, and the crude linear peptide was washed with diethyl ether. The peptide was immediately dissolved in 200 ml of 25% acetonitrile/10% TFA (aq) and oxidised as described supra. The resulting mixture was loaded directly onto an HPLC column and purified using triethylammonium phosphate buffer at pH 2.3. The subsequent purification steps were identical to the procedure for compound 1. 41 mg (~10% yield) of white amorphous powder was obtained. HPLC: Rt=10.0 min, gradient: 20→40% B over 20 min, t=40° C., solvent A 0.01% TFA (aq), solvent B 70% $CH_3CN$, 0.01% TFA (aq); Purity: 100%; MS ($M+H^+$): expected 992.5, observed 992.2.

The other compounds were prepared by analogous variation of these synthetic procedures.

Experimental (Biological Testing)

In vitro receptor assays:

Agonist activity of compounds on the hV1a receptor was determined in a transcriptional reporter assay by transiently transfecting a hV1a receptor expression DNA into HEK-293 cells in concert with a reporter DNA containing intracellular calcium responsive promoter elements regulating expression of firefly luciferase. See Boss, V., Talpade, D. J., Murphy, T. J. *J. Biol. Chem.* 1996, May 3; 271(18), 10429-10432 for further guidance on this assay. Cells were exposed to serial dilutions of compounds diluted 10-fold per dose for 5 hours, followed by lysis of cells, determination of luciferace activity, and determination of compound efficacies and $EC_{50}$ values through non-linear regression. Arginine-vasopressin (AVP) was used as an internal control in each experiment, and compounds were tested in at least three independent experiments. To determine selectivity, compounds were tested in luciferase-based transcriptional reporter assays expressing the human oxytocin (hOT) receptor. Assays for other receptors (hV2, hV1b, rat V1a and rat V2) were also conducted.

For further comparative purposes, other reference compounds used were [Phe2,Orn8]OT, terlipressin and F180.

The structure of [Phe2,Orn8]OT is:

(SEQ ID NO: 51)

H-Cys-Phe-Ile-Gln-Asn-Cys-Pro-Orn-Gly-$NH_2$.
|_____|

The structure of F180 is:

(SEQ ID NO: 52)

Hmp-Phe-Ile-Hgn-Asn-Cys-Pro-Dbu(Abu)-Gly-$NH_2$.
|_____|

The results of the in vitro assays are depicted in table 2 infra. The $EC_{50}$ value given is the geometric mean expressed in nanomol/L (nM). Selectivity values are given as $EC_{50}$ ratios.

In Vivo Pharmacological Tests:

The compounds were tested in vivo for duration of action related to a standard dose of AVP. Blood pressure tests were carried out on anaesthetised Sprague-Dawley male rats (weighing 270-300 g) with catheterised jugular vein and carotid artery. The catheterised carotid artery was used to continuously monitor blood pressure and the jugular vein was used for administration of the compounds tested. Rats received intravenous injections of dibenamine prior to dosing to enhance their responsiveness to V1a receptor agonists (cf. Dekanski, J., *Br. J. Pharmacol.* 1952, 7, 567-572). The dosing procedure consisted of one intravenous injection of physiological saline followed by two consecutive injections of a standard dose of AVP (0.1 nmol/kg, ≈$ED_{70}$), and three to five increasing doses of a given compound selected to give at least a response comparable to the standard dose of AVP. Dosing intervals were set as time for the blood pressure to decrease to a stable baseline.

Determination of duration of action was based on the decay rate of diastolic arterial blood pressure transient increase. Specifically, for an exponential decay of plasma concentration, it can be shown that, if the response is measured beyond the distribution phase, the rate of decay near the $EC_{50}$ is linear and inversely proportional to the elimination half-life (Rowland, M. and Tozer, T. in "*Clinical Pharmacokinetics, Concepts and Applications*", $3^{rd}$ ed., Lippincott Williams & Wilkins, Philadelphia, 1995).

To measure the response decay rate for a given compound, a dose was selected that gave an amplitude of response as similar as possible to the amplitude of response to the second injection of the standard dose of AVP. To normalise for inter-individual variation in V1a-responsiveness, the duration of action was expressed as the ratio of decay rate for this reference AVP response to the decay rate for the equieffective dose of compound for each rat tested. The results obtained for the compounds tested are set forth in table 2.

TABLE 2

Results of biological testing

| Compound tested | $EC_{50}$ hV1a receptor (nM) | in vivo duration relative to AVP | selectivity hOT/hV1a |
|---|---|---|---|
| 8 | 0.50 | – | 11 |
| 9 | 0.68 | 1.5 | + |
| 10 | 1.15 | 2.3 | 11 |
| 11 | 2.96 | 1.9 | + |
| 12 | 24.96 | – | + |
| 13 | 18.77 | – | + |
| 14 | 0.54 | – | 75 |
| 15 | 0.61 | 2.2 | 43 |
| 16 | 11.88 | – | + |
| 17 | 30.29 | – | + |
| 18 | 29.85 | – | + |
| 19 | 5.99 | 1.6 | + |
| 20 | 39.28 | – | + |
| 21 | 20.66 | – | + |
| 1* | 2.02 | 1.7 | + |
| 22 | 18.13 | – | + |

TABLE 2-continued

Results of biological testing

| Compound tested | $EC_{50}$ hV1a receptor (nM) | in vivo duration relative to AVP | selectivity hOT/hV1a |
|---|---|---|---|
| 23 | 7.97 | – | + |
| 24 | 4.09 | – | + |
| 25 | 1.40 | 2.0 | 23 |
| 2* | 1.18 | 1.7 | + |
| 26 | 2.24 | 2.0 | 28 |
| 27 | 16.21 | – | + |
| 28 | 5.17 | – | + |
| 29 | 4.77 | – | + |
| 30 | 1.45 | 1.7 | + |
| 3* | 1.47 | 1.7 | + |
| 31 | 3.91 | – | + |
| 4* | 2.36 | 1.8 | + |
| 32 | 2.64 | 2.1 | 35 |
| 33 | 14.61 | – | + |
| 5* | 0.25 | 1.9 | 117 |
| 34 | 0.73 | 2.0 | 72 |
| 35 | 7.30 | – | + |
| 36 | 11.54 | – | + |
| 37 | 7.45 | – | + |
| 38 | 10.11 | – | + |
| 39 | 0.21 | 1.9 | 178 |
| 40 | 0.27 | 2.0 | 88 |
| 41 | 0.98 | 2.6 | 53 |
| 42 | 6.25 | – | + |
| 43 | 13.71 | – | + |
| 44 | 14.48 | – | + |
| 6* | 0.29 | 1.9 | 86 |
| 45 | 1.65 | – | 18 |
| 46 | 2.41 | 2.1 | + |
| 47 | 0.99 | 1.6 | + |
| 7* | 2.84 | – | + |
| 48 | 5.70 | – | + |
| 49 | 3.58 | – | + |
| 50 | 1.52 | 2.4 | 43 |
| [Phe2, Orn8]OT | 0.15 | 1.9 | 60 |
| terlipressin | 82.08 | 9.1 | + |
| AVP | 0.21 | 0.9 | 108 |
| F180 | 0.56 | 3.8 | + |

– = not tested
+ = selective hV1a receptor agonist; $EC_{50}$ hOT/hV1a ratio not determined due to very low agonist efficacy (<30% compared to AVP) at the hOT receptor All references listed are to be regarded as an integral part of the present writ and, hence, are incorporated by reference.

The invention claimed is:

1. A method of treating a condition selected from:
hypertensive gastropathy bleeding;
prolonged and severe hypotension;
intradialytic hypotension;
vasodilatory shock induced by cardio-pulmonary bypass;
milrinone-induced vasodilatory shock in congestive heart failure;
anaphylactic shock;
cardiovascular instability induced by brain death;
acute respiratory distress syndrome;
acute lung injury;
shock induced by metformin intoxication, mitochondrial disease, cyanide poisoning, or by vascular leak syndrome induced by interleukin-2 or another cytokine, denileukin diftitox or another immunotoxin, or ovarian hyperstimulation syndrome;
hypertension induced by end-stage renal disease;
irritable bowel disease;
reperfusion injury;
infant respiratory distress syndrome;
severe acute respiratory syndrome;
ascites;
vasodepressor syncope;
toxic shock syndrome; and
idiopathic systemic capillary leak syndrome (Clarkson's disease);
wherein the method comprises administering to an animal patient in need of such treatment a therapeutically effective amount of a compound having the formula (I):

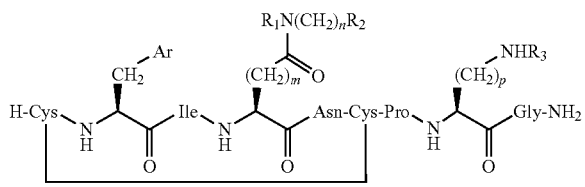

(SEQ ID NO: 53)

wherein:
Ar is an aryl group selected from aromatic carbocyclic ring systems, five- or six-membered heteroaromatic ring systems and bicyclic heteroaromatic ring systems;
m is selected from 1, 2 and 3;
n is selected from 0, 1, 2, 3 and 4;
p is selected from 2, 3 and 4;
$R_1$, $R_2$ and $R_3$ are independently selected from H, OH, alkyl, O-alkyl and OC(O)-alkyl;
alkyl is selected from $C_{1-6}$ straight and $C_{4-8}$ branched chain alkyl and optionally has at least one hydroxyl substituent;
and when n=0, $R_1$ and $R_2$ optionally together form a nitrogen containing ring structure comprising from 2 to 5 carbon atoms;
with the proviso that when Ar is phenyl, m=2, n=0, $R_1$=$R_2$=H, and p is 3 or 4, $R_3$ is not H;
or a pharmaceutically acceptable salt thereof or a solvate thereof.

2. The method as defined in claim 1 wherein the condition comprises acute respiratory distress syndrome or acute lung injury.

3. The method as defined in claim 1 wherein the condition comprises:
shock induced by metformin intoxication, mitochondrial disease, cyanide poisoning, or by vascular leak syndrome induced by interleukin-2 or another cytokine, denileukin diftitox or another immunotoxin, or ovarian hyperstimulation syndrome;
hypertension induced by end-stage renal disease;
irritable bowel disease;
reperfusion injury;
infant respiratory distress syndrome;
severe acute respiratory syndrome;
ascites;
vasodepressor syncope;
toxic shock syndrome; or
idiopathic systemic capillary leak syndrome (Clarkson's disease).

4. The method according to claim 1, wherein Ar is selected from phenyl, 2- or 3-thienyl, 2- or 3-furyl, 2-, 3- or 4-pyridyl and 2-, 4- or 5-thiazolyl.

5. The method according to claim 1, wherein $R_1$ is H.

6. The method according to claim 1, wherein p is 2 or 3.

7. The method according to claim 1, wherein $R_2$ is selected from H, OH, $CH_3$, $CH_2CH_3$, $CH(CH_3)_2$, $CH(CH_2OH)_2$, $CH(OH)CH_3$, $OCH_3$ and $OCH_2CH_2OH$.

8. The method according to claim 1, wherein $R_3$ is selected from H, methyl, ethyl, n-propyl, i-propyl and i-amyl.

9. The method according to claim 1, wherein the compound is selected from the group consisting of:

(SEQ ID NO: 1)
H-Cys-Phe-Ile-Hgn-Asn-Cys-Pro-Orn(i-Pr)-Gly-NH₂;

(SEQ ID NO: 2)
H-Cys-Phe-Ile-Asn((CH₂)₃OH)-Asn-Cys-Pro-Orn-Gly-NH₂;

(SEQ ID NO: 3)
H-Cys-Phe-Ile-Asn-Asn-Cys-Pro-Dbu-Gly-NH₂;

-continued (SEQ ID NO: 4)

H-Cys-Phe-Ile-Asn(CH₂CH₃)-Asn-Cys-Pro-Dbu-Gly-NH₂;

(SEQ ID NO: 5)

H-Cys-Phe-Ile-Gln-Asn-Cys-Pro-Orn(i-Pr)-Gly-NH₂;

(SEQ ID NO: 6)

H-Cys-Phe-Ile-Gln-Asn-Cys-Pro-Orn(CH₂CH₃)-Gly-NH₂; and

(SEQ ID NO: 7)

H-Cys-Phe-Ile-Asn(CH₃)₂-Asn-Cys-Pro-Orn-Gly-NH₂;
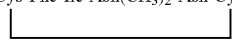

and pharmaceutically acceptable salts thereof.

10. The method of claim 1, wherein the animal patient is a human.

11. The method of claim 1, wherein the condition is anaphylactic shock.

12. The method according to claim 1, wherein the compound is:

(SEQ ID NO: 1)

H-Cys-Phe-Ile-Hgn-Asn-Cys-Pro-Orn(i-Pr)-Gly-NH₂;
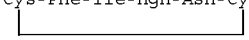

or a pharmaceutically acceptable salt thereof.

13. The method according to claim 1, wherein the compound is:

(SEQ ID NO: 2)

H-Cys-Phe-Ile-Asn((CH₂)₃OH)-Asn-Cys-Pro-Orn-Gly-NH₂;

or a pharmaceutically acceptable salt thereof.

14. The method according to claim 1, wherein the compound is:

(SEQ ID NO: 3)

H-Cys-Phe-Ile-Asn-Asn-Cys-Pro-Dbu-Gly-NH₂;

or a pharmaceutically acceptable salt thereof.

15. The method according to claim 1, wherein the compound is:

(SEQ ID NO: 4)

H-Cys-Phe-Ile-Asn(CH₂CH₃)-Asn-Cys-Pro-Dbu-Gly-NH₂;

or a pharmaceutically acceptable salt thereof.

16. The method according to claim 1, wherein the compound is:

(SEQ ID NO: 5)

H-Cys-Phe-Ile-Gln-Asn-Cys-Pro-Orn(i-Pr)-Gly-NH₂;

or a pharmaceutically acceptable salt thereof.

17. The method according to claim 1, wherein the compound is:

(SEQ ID NO: 6)

H-Cys-Phe-Ile-Gln-Asn-Cys-Pro-Orn(CH₂CH₃)-Gly-NH₂;

or a pharmaceutically acceptable salt thereof.

18. The method according to claim 1, wherein the compound is:

(SEQ ID NO: 7)

H-Cys-Phe-Ile-Asn(CH₃)₂-Asn-Cys-Pro-Orn-Gly-NH₂;

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,222,202 B2 | Page 1 of 1 |
| APPLICATION NO. | : 12/223673 | |
| DATED | : July 17, 2012 | |
| INVENTOR(S) | : Laporte et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 686 days.

Signed and Sealed this
Twenty-seventh Day of November, 2012

David J. Kappos
*Director of the United States Patent and Trademark Office*

UNITED STATES PATENT AND TRADEMARK OFFICE
CERTIFICATE OF CORRECTION

PATENT NO. : 8,222,202 B2  Page 1 of 1
APPLICATION NO. : 12/223673
DATED : July 17, 2012
INVENTOR(S) : Regent LaPorte and Pierre J. M. Riviere It is certified that error appears in the above-identified patent and that said Letters Patent is hereby corrected as shown below:

Title Page, Item (57)
(Abstract), Line 8, delete "(1)," and insert -- (I), --.

Signed and Sealed this
Twenty-eighth Day of May, 2013

Teresa Stanek Rea
*Acting Director of the United States Patent and Trademark Office*